United States Patent
Harada (10) Patent No.: US 7,288,226 B2
(45) Date of Patent: Oct. 30, 2007

(54) AUTOMATIC METAL SOLUTION DILUTOR

(75) Inventor: Yoshinori Harada, Kashihara (JP)

(73) Assignee: Sharp Kabushiki Kaisha, Osaka (JP)

( * ) Notice: Subject to any disclaimer, the term of this patent is extended or adjusted under 35 U.S.C. 154(b) by 668 days.

(21) Appl. No.: 10/626,084

(22) Filed: Jul. 23, 2003

(65) Prior Publication Data

US 2004/0244506 A1    Dec. 9, 2004

(30) Foreign Application Priority Data

Aug. 23, 2002 (JP) .............................. 2002-243824

(51) Int. Cl.
*G01N 15/06* (2006.01)
(52) U.S. Cl. .................. 422/68.1; 422/63; 422/64; 422/65; 422/99; 422/100; 436/180
(58) Field of Classification Search ............... 73/19.01; 422/99–101, 63–65, 68.1; 436/180
See application file for complete search history.

(56) References Cited

U.S. PATENT DOCUMENTS 4,465,554 A * 8/1984 Glass ................ 159/16.1

FOREIGN PATENT DOCUMENTS

| JP | 04-124451 | 11/1992 |
|----|-----------|---------|
| JP | 06-307994 | 11/1994 |
| JP | 06-307994 A | 11/1994 |
| JP | 07167756 | * 4/1995 |
| JP | 07-167756 | 7/1995 |
| JP | 07-167756 A | 7/1995 |
| JP | 08-184540 | 7/1996 |
| JP | 10-221229 | 8/1998 |
| JP | 2001-305025 | 10/2001 |

* cited by examiner

*Primary Examiner*—Jill Warden
*Assistant Examiner*—Jyoti Nagpaul
(74) *Attorney, Agent, or Firm*—David G. Conlin; David A. Tucker; Edwards Angell Palmer & Dodge LLP (57) ABSTRACT

In an automatic metal solution dilutor according to the present invention, a densitometer (absorptiometer) measures absorbance of a diluted solution in a metering hopper. An electronic balance meters the diluted solution in the metering hopper so that a dilution magnification obtained from the absorbance reaches a prescribed value. A control part monitors the value measured by the densitometer and the value metered by the electronic balance for operating and controlling the quantity of a stock solution/diluent liquid fed to the metering hopper so that the dilution magnification reaches the prescribed value on the basis of the absorbance measured by the densitometer. Thus obtained is an automatic metal solution dilutor capable of diluting a concentrated liquid of the order of percentage to a metal solution of the order of ppm having a required quantity and a required concentration and correctly feeding the same to a feeder while performing in-line concentration control.

5 Claims, 8 Drawing Sheets

CORRELATION BETWEEN ABSORPTIOMETER AND ICP-AES

AUTOMATIC METAL SOLUTION DILUTOR

BACKGROUND OF THE INVENTION

1. Field of the Invention

The present invention relates to an automatic metal solution dilutor, and more particularly, it relates to an automatic metal solution dilutor automatically diluting a concentrated metal solution from the order of percentage to the order of ppm in high accuracy.

2. Description of the Background Art

According to a general dilution method, an object metal pulverulent body or a concentrated metal solution of the order of percentage is manually metered, mixed with a diluent liquid to be diluted to a required concentration and a required quantity, and fed to a feeder.

However, this method employs an around-the-clock system and dilution errors result from manual dilution by a plurality of operators. The metal pulverulent body or the metal solution is not fed with in-line concentration control, and hence concentration fluctuation caused by manual dilution errors or unexpected inclusion of water resulting from an equipment failure or breakdown leads to sudden concentration abnormality such that the diluted solution cannot be stably fed to the feeder by 100%.

In concentration measurement, a high-quality analyzer such as an atomic absorption spectrophotometer or an ICP analyzer is employed for analyzing the metal concentration of the order of ppm (parts per million: $10^{-6}$). Such a high-quality analyzer must be set in a humidity-controlled control room or the like under an excellent environmental condition in consideration of assurance of analytical accuracy or management of the analyzer, and a measured solution must be diluted to the order of ppb (parts per billion: $10^{-9}$).

A method of concentration measurement employing neutralization titration is also carried out. However, this method requires a large-scale apparatus and a long time for concentration measurement. When a liquid dilution tank of at least several 10 liters is provided, therefore, this method can be employed with no problem. However, it is difficult to apply this method to a dilutor non-periodically feeding a diluted solution having a required concentration and a required quantity.

The following techniques disclosed in Japanese Patent Laying-Open Nos. 6-307994 (1994) and 7-167756 (1995) have been confirmed as conventional dilutors:

Japanese Patent Laying-Open No. 6-307994 discloses a dilutor diluting a fed stock solution mixed with a diluent liquid in a vessel and feeding the diluted solution to a remote measuring device with compressed gas.

The technique disclosed in this gazette relates to a liquid dilutor applied for diluting a liquid having a high metal ion concentration readily depositing crystals. According to this technique, the diluent liquid and a concentrated liquid are metered, thereafter fed, stirred/diluted in a tank and fed to a feeder with compressed air after completion of the dilution.

Japanese Patent Laying-Open No. 7-167756 discloses a method of inputting absorbance of a stock solution and a diluent liquid with a densitometer measuring absorbance or the like, operating a dilution magnification for the liquid to be diluted with the diluent liquid and diluting the liquid without requiring strict measurement of the volume or the weight.

The technique disclosed in this gazette relates to an automatic liquid dilutor applied to water treatment chemicals for a power plant or the like. This technique employs a method of calculating a dilution ratio from a result of measurement with the densitometer performing calculation with reference to absorbance.

According to the dilutor disclosed in Japanese Patent Laying-Open No. 6-307994, however, it is difficult to accurately meter a required liquid volume due to a metering method of introducing and charging the stock solution and the diluent liquid in a meter of a constant volume and thereafter feeding the same to a dilution tank.

Further, this method depends on only metering without executing concentration control, disadvantageously leading to inferior reliability of the prepared diluted solution.

The apparatus disclosed in Japanese Patent Laying-Open No. 7-167756 dilutes ammonia to the order of ppb, and hence it is disadvantageously necessary to add a 1% ethanol solution serving as an index substance.

In this analyzer executing weighing only through a valve switching time, weighing is so dispersed that stable dilution cannot be performed.

SUMMARY OF THE INVENTION

An object of the present invention is to provide an automatic metal solution dilutor capable of correctly diluting a concentrated liquid of the order of percentage to a metal solution of the order of ppm having a required quantity and a required concentration and correctly feeding the metal solution to a feeder while performing in-line concentration control.

The automatic metal solution dilutor according to the present invention comprises a material feeding part, a dilution tank, a measuring device, a metering device and a control part. The material feeding part stores a stock solution to be diluted. In order to dilute the stock solution, the dilution tank mixes the stock solution fed from the material feeding part with a diluent liquid for preparing a diluted solution. The measuring device measures absorbance of the diluted solution in the dilution tank. The metering device meters the diluted solution in the dilution tank with an electronic balance so that a dilution magnification obtained from the absorbance measured by the measuring device reaches a prescribed value. The control part monitors the value measured by the measuring device and the value metered by the metering device for operating and controlling the quantity of at least either the stock solution or the diluent liquid fed to the dilution tank so that the dilution magnification reaches the prescribed value on the basis of the absorbance measured by the measuring device.

According to the inventive automatic metal solution dilutor, it is possible to correctly dilute a concentrated liquid (stock solution) of the order of percentage to a metal solution of the order of ppm having a required quantity and a required concentration with no dilution error by measuring the absorbance of the diluted solution in the dilution tank and metering the diluted solution in the dilution tank with the electronic balance of the metering device so that the dilution magnification reaches the prescribed value on the basis of the measured absorbance.

The control part monitors the values measured by the measuring device and metered by the metering device respectively for operating and controlling the quantity of the stock solution and/or the diluent liquid fed to the dilution tank on the basis thereof, whereby it is possible to continuously and automatically measure and monitor the dilution magnification and the quantity of preparation.

The concentration of the diluted solution, which is measured with an absorptiometer manufacturable at a low cost, may not be subjected to off-line testing with a high-quality analyzer such as a high-priced atomic absorption spectrophotometer or an ICP analyzer. Further, the electronic balance enables metering with resolution higher than that of a load cell by at least one digit due to weighing.

Thus, it is possible to provide an automatic dilutor implementing accurate dilution of a metal solution at a low cost.

Further, a specified quantity of the stock solution is diluted according to a gravimetric method, whereby no error results from fluctuation of the liquid temperature but anybody can accurately dilute the stock solution with no requirement for experiences and skillfulness dissimilarly to a manual operation. Thus, the dilutor causes no human error and the concentration and the results of weighing and measurement can be readily confirmed due to monitor display with a required concentration and a required quantity while it is possible to prepare a diluted solution with a concentration and a quantity required by the feeder side, whereby the feeder side can effectively take flexible countermeasures.

The aforementioned automatic metal solution dilutor preferably further comprises a finishing part having several tanks including mechanisms of storing the diluted solution fed from the dilution tank and feeding the diluted solution with compressed gas.

Thus, the finishing part can also feed the diluted solution with no contaminants.

In the aforementioned automatic metal solution dilutor, the material feeding part preferably includes an exchangeable bottle for storing the stock solution and has a structure feeding the stock solution stored in the bottle to the dilution tank with compressed gas.

Thus, the degree of contamination can be reduced and metal dilution can be further accurately performed to the order of ppm.

In the aforementioned automatic metal solution dilutor, the dilution tank preferably has a purging mechanism incorporating compressive gas inward and discharging the compressive gas outward.

Thus, no contaminants are mixed into the diluted solution so that the diluted solution can be fed with no impurity.

The aforementioned automatic metal solution dilutor preferably further comprises a hopper having the purging mechanism incorporating the compressive gas inward and discharging the compressive gas outward in a path for feeding the diluted solution from the dilution tank, and a pipe connecting the dilution tank and the measuring device with each other is preferably at least partially formed by a spiral tube.

Thus, an influence exerted on the metering device by the pipe feeding the diluted solution from the dilution tank can be reduced.

In the aforementioned automatic metal solution dilutor, at least two pipes having different thicknesses preferably introduce the diluent liquid into the dilution tank.

When the diluent liquid is introduced through at least two pipes having different thicknesses, stirring naturally takes place and hence no stirring member may be separately provided. Further, it is possible to implement introduction control as accurately as possible by employing the larger pipe for increasing the feeding speed to some extent and improving the effect of stirring while employing the smaller pipe for correctly introducing the diluent liquid by a target quantity.

In the aforementioned automatic metal solution dilutor, the material for portions coming into contact with the stock solution, the diluent liquid and the diluted solution consists of resin containing a low amount of fluorine.

Thus, no metal comes into contact with the stock solution, the diluent liquid and the diluted solution, whereby the quantity of metal contaminants can be reduced and metal dilution can be further accurately performed to the order of ppm.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention are now described with reference to the drawings.

First Embodiment

Figure 1:
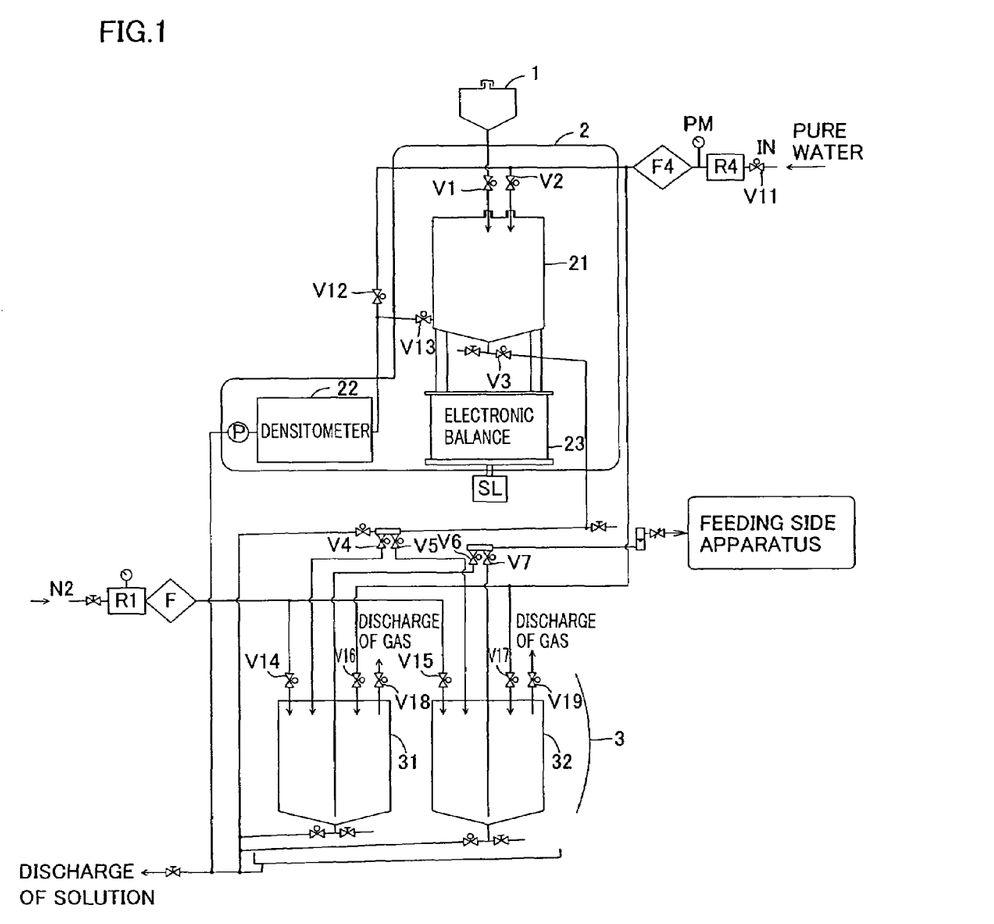
FIG. 1 is a general pipe system diagram showing the structure of an automatic metal solution dilutor according to a first embodiment of the present invention.

Referring to FIG. 1, an automatic metal solution dilutor according to a first embodiment of the present invention, adding a liquid to a metering hopper 21 while confirming the residue of a stock solution, mainly includes a material feeding part 1, a preparation part 2, a finishing part 3 and a control part (not shown).

The material feeding part 1 stores the stock solution to be diluted and feeds the stock solution to the preparation part 2.

The preparation part 2 has the metering hopper 21 serving as a dilution tank, a densitometer 22 serving as a measuring device and an electronic balance 23 serving as a metering device. The metering hopper 21, mixing the stock solution fed from the material feeding part 1 with a diluent liquid and preparing a diluted solution for diluting the stock solution, is not closed. The material feeding part 1 feeds the stock solution to the metering hopper 21 through a pipe having a valve V1 while the diluent liquid (pure water, for example) is fed to the metering hopper 21 through a pipe having a valve V2.

The densitometer 22 serving as an absorptiometer measuring absorbance of the diluted solution in the metering hopper 21 employs such a principle that the ultraviolet spectrum of the object solution varies with the concentration of the component forming the same. The diluent liquid is fed to the densitometer 22 through a pipe having a valve V12, while the metering hopper 21 feeds the diluted solution to the densitometer 22 through a pipe having a valve V13.

The electronic balance 23 meters the diluted solution in the metering hopper 21 so that a dilution magnification obtained from the absorbance measured by the densitometer 22 reaches a prescribed value.

The finishing part 3 has several closed tanks 31 and 32 including mechanisms for storing the diluted solution fed from the metering hopper 21 and feeding the same with compressed gas. The metering hopper 21 feeds the diluted solution to each of the closed tanks 31 and 32 through a pipe having a valve V3 and another pipe, branched therefrom, having a valve V4 or V5. A pipe having a valve V14 or V15 supplies high-pressure gas (nitrogen, for example) to each of the closed tanks 31 and 32. A pipe having a valve V18 or V19 connected to each of the closed tanks 31 and 32 discharges the high-pressure gas supplied thereto outward. Each of the closed tanks 31 and 32 is supplied with the high-pressure gas in the aforementioned manner, thereby feeding the diluted solution stored therein to a feeding side apparatus through a pipe having a valve V6 or V7.

The control part monitors the value measured by the densitometer 22 and the value metered by the electronic balance 23 for operating and controlling the quantity of at least either the stock solution or the diluent liquid fed to the metering hopper 21 so that the dilution magnification reaches the prescribed value on the basis of the absorbance measured by the densitometer 22. The control part controls the quantity of the stock solution or the diluent liquid to the metering hopper 21 in response to the aperture of the valve V1 or V2, for example.

The diluted solution measured by the densitometer 22, that fed from the metering hopper 21 to the closed tanks 31 and 32 and that in the closed tanks 31 and 32 are properly discharged.

The automatic metal solution dilutor according to the first embodiment is different from the dilutor disclosed in Japanese Patent Laying-Open No. 6-307994 in the following points:

(1) While the dilutor disclosed in the aforementioned gazette performs stirring/dilution with a stirrer, the dilutor according to this embodiment has no stirring mechanism in consideration of prevention of dusting and inclusion of air.

(2) While the dilutor disclosed in the aforementioned gazette executes dilution in a closed vessel, the dilutor according to this embodiment executes no dilution in a closed vessel.

(3) While the dilutor disclosed in the aforementioned gazette introduces and charges the stock solution and the diluent liquid in the meter having a constant volume and thereafter feeds the same to the dilution tank, the dilutor according to this embodiment executes metering with the electronic balance 23 for accurately metering a required quantity of liquid.

(4) While the dilutor disclosed in the aforementioned gazette executes no concentration control, the dilutor according to this embodiment executes concentration control in addition to metering, for improving reliability of the prepared diluted solution.

Further, the automatic metal solution dilutor according to the first embodiment is different from the apparatus disclosed in Japanese Patent Laying-Open No. 7-167756 in the following points:

(1) While the apparatus disclosed in the aforementioned gazette dilutes ammonia, the dilutor according to this embodiment dilutes a metal solution.

(2) While the apparatus disclosed in the aforementioned gazette adds the 1% ethanol solution serving as an index substance for diluting ammonia to the order of ppb, the dilutor according to this embodiment diluting the metal solution to the order of ppb requires no additional solution.

(3) While the apparatus disclosed in the aforementioned gazette executes weighing through the valve switching time, the weighing is so dispersed that ammonia cannot be stably diluted in this case. The dilutor according to this embodiment executes control and accurate weighing with a gravimeter and employs at least two types of pipe diameters in a path for introducing the diluent liquid as described later for controlling the quantity of introduction. In relation to the valve switching time, further, this dilutor implements accurate weighing through an additional operation such as a one-shot mode operation of switching the valves while setting the unit time to 0.1 sec.

(4) The apparatus disclosed in the aforementioned gazette dilutes ammonia only through concentration measurement and valve switching without confirming correctness of the quantity of the actually introduced liquid by weighing dissimilarly to the dilutor according to this embodiment.

(5) The aforementioned gazette describes that the diluted solution contains no dissolved solid such as a metal or salt, while the dilutor according to this embodiment is directed to a metal.

Thus, the automatic metal solution dilutor according to this embodiment attains the following functions/effects:

It is possible to correctly dilute a concentrated liquid (stock solution) of the order of percentage to a metal solution of the order of ppm having a required quantity and a required concentration with no dilution error by measuring the absorbance of the diluted solution in the metering hopper 21 with the densitometer 22 and metering the diluted solution in the dilution tank with the electronic balance 23 so that the dilution magnification reaches the prescribed value on the basis of the measured absorbance.

The control part monitors the values measured by the densitometer 22 and metered by the electronic balance 23 for operating and controlling the quantities of the stock solution and the diluent liquid fed to the metering hopper 21 on the basis thereof, whereby the dilution magnification and the quantity of preparation can be continuously and automatically measured and monitored.

The concentration of the diluted solution, which is measured with the absorptiometer 22 manufacturable at a low cost, may not be subjected to off-line testing with a high-quality analyzer such as a high-priced atomic absorption spectrophotometer or an ICP analyzer. Further, the electronic balance 23 enables metering with resolution higher than that of a load cell by at least one digit due to weighing.

Thus, it is possible to provide an automatic dilutor implementing accurate dilution of a metal solution at a low cost.

Further, a specified quantity of the stock solution is diluted according to a gravimetric method, whereby no error results from fluctuation of the liquid temperature but anybody can accurately dilute the stock solution with no requirement for experiences and skillfulness dissimilarly to a manual operation. Thus, the dilutor causes no human error and the concentration and the results of weighing and measurement can be readily confirmed due to monitor display with a required concentration and a required quantity while it is possible to prepare a diluted solution with a concentration and a quantity required by the feeder side, whereby the feeder side can effectively take flexible countermeasures.

Second Embodiment

Figure 2:
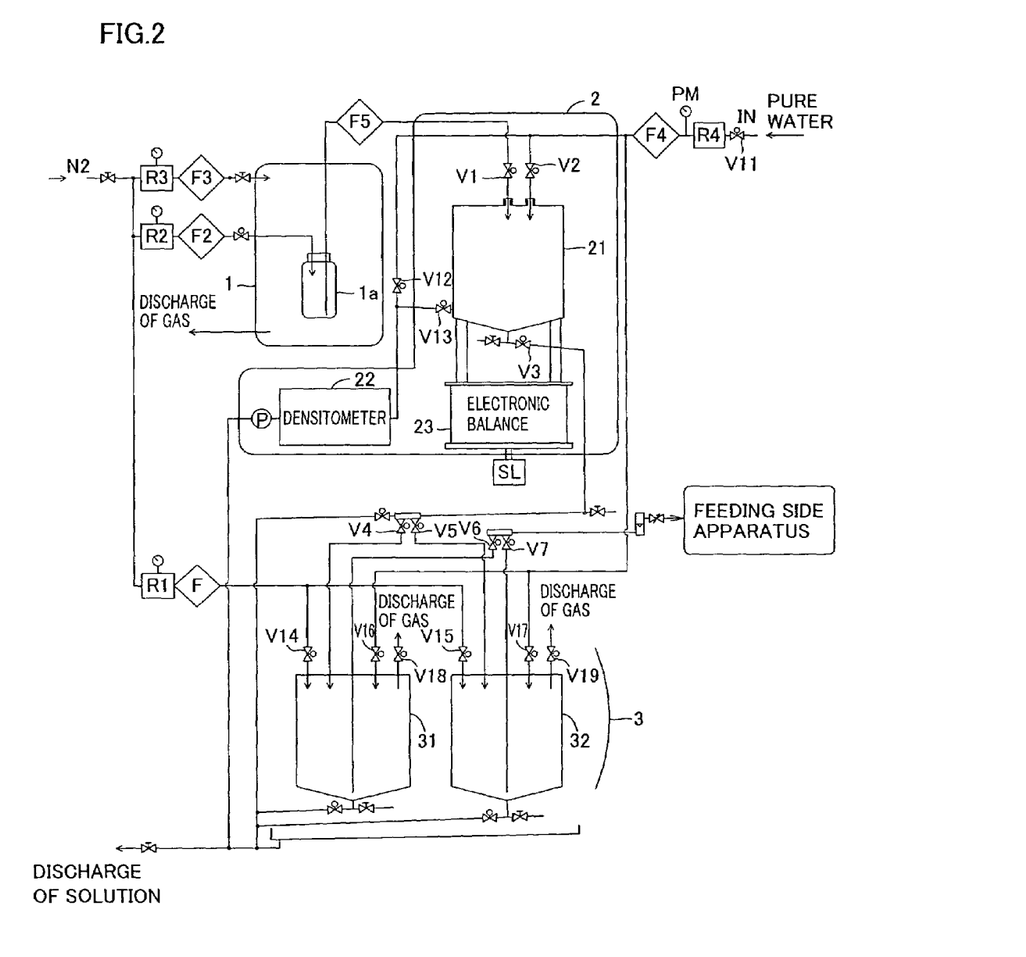
FIG. 2 is a general pipe system diagram showing the structure of an automatic metal solution dilutor according to a second embodiment of the present invention.

Referring to FIG. 2, the structure of an automatic metal solution dilutor according to a second embodiment of the present invention is different from that shown in FIG. 1 in a point that a material feeding part 1 includes an exchangeable bottle 1a capable of storing a stock solution of 500 cc, for example, and has a structure feeding the stock solution stored in the bottle 1a to a metering hopper 21 by applying pressure with compressed gas (nitrogen, for example).

The remaining structure of the automatic metal solution dilutor according to the second embodiment is substantially identical to that shown in FIG. 1. Therefore, members identical to those shown in FIG. 1 are denoted by the same reference numerals, and redundant description is not repeated.

According to this embodiment, the bottle 1a is refillable and the stock solution stored therein is fed with compressed gas, whereby no contaminants are mixed into the stock solution, and solution leakage resulting from a manual operation, damage on an operator caused by splash in additional introduction of the stock solution, solution leakage or the like can be eliminated.

Third Embodiment

Figure 3:
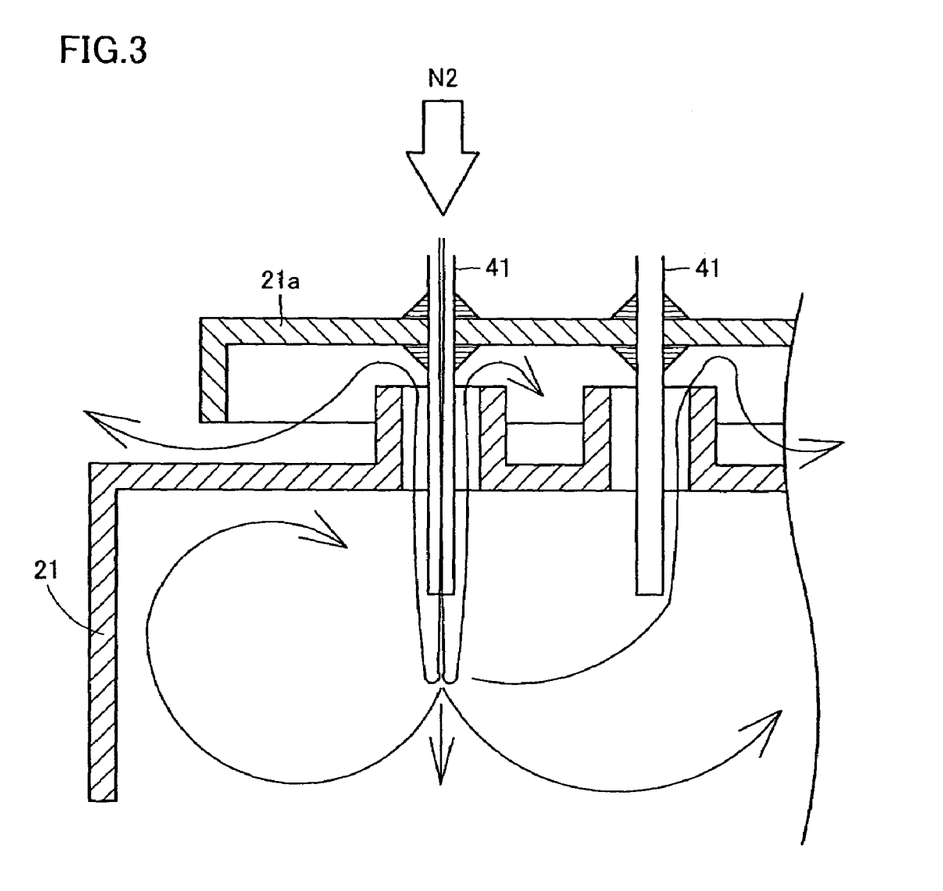
FIG. 3 is a partially fragmented sectional view showing the structure of a metering hopper in an automatic metal solution dilutor according to a third embodiment of the present invention.

Referring to FIG. 3, the structure of an automatic metal solution dilutor according to a third embodiment of the present invention is different from those according to the first and second embodiments in a point that a metering hopper 21 includes an $N_2$ purging mechanism on a lid 21a.

Pipes 41 for feeding nitrogen ($N_2$) gas are fixed to the lid 21a and inserted into holes of the metering hopper 21 with clearances. Thus, the forward ends of the pipes 41 reach the inner part of the metering hopper 21. Further, a clearance is defined between the lid 21a and the upper surface of the metering hopper 21. Thus, the nitrogen gas fed into the metering hopper 21 through the pipes 41 is discharged from the metering hopper 21 through the clearances between the pipes 41 and the holes and the clearance between the lid 21a and the upper surface of the metering hopper 21.

The remaining structure of the automatic metal solution dilutor according to the third embodiment is substantially identical to that shown in FIG. 1 or FIG. 2. Therefore, members identical to those shown in FIG. 1 or FIG. 2 are denoted by the same reference numerals, and redundant description is not repeated.

According to this embodiment, the metering hopper 21 includes the $N_2$ purging mechanism on the lid 21a, whereby no contaminants are mixed into a diluted solution so that the diluted solution can be fed with no impurities.

Fourth Embodiment

Figure 4:
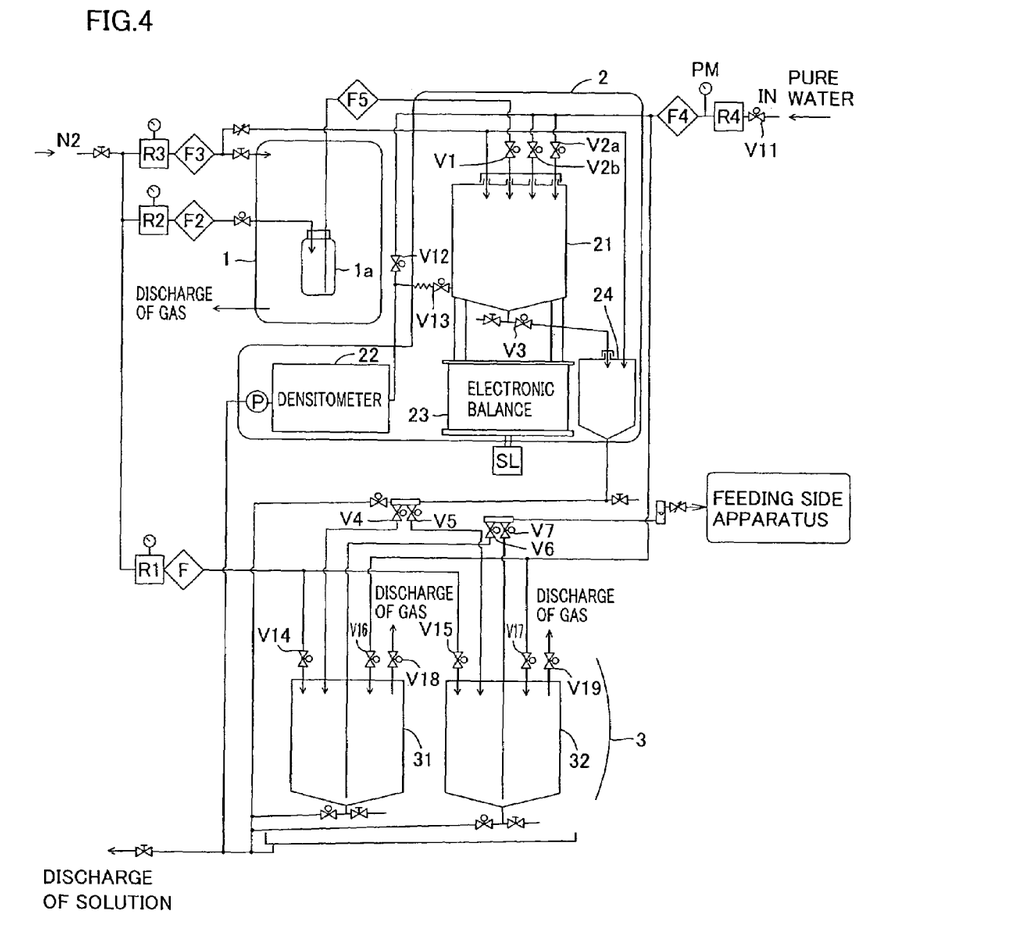
FIG. 4 is a general pipe system diagram showing the structure of an automatic metal solution dilutor according to a fourth embodiment of the present invention.

Referring to FIG. 4, a hopper 24 including a mechanism for preventing contamination by $N_2$ purging is arranged on a path for feeding a liquid from a metering hopper 21 to a finishing part 3 in an automatic metal solution dilutor according to a fourth embodiment of the present invention. A pipe having a valve V3 and another pipe are connected to the hopper 24 for feeding a diluted solution and nitrogen gas thereto respectively. The nitrogen gas fed into the hopper 24 is discharged therefrom by a structure similar to that shown in FIG. 3.

A pipe, having a valve V13, connecting the metering hopper 21 and a densitometer 22 with each other is at least partially formed by a spiral tube. A diluent liquid is fed to the metering hopper 21 in a branched manner through two pipes having valves V2a and V2b respectively. The metering hopper 21 has an $N_2$ purging mechanism similar to that shown in FIG. 3.

The remaining structure of the automatic metal solution dilutor according to the fourth embodiment is substantially identical to that shown in FIG. 2. Therefore, members identical to those shown in FIG. 2 are denoted by the same reference numerals, and redundant description is not repeated.

According to this embodiment, the hopper 24 includes the mechanism for preventing contamination by $N_2$ purging while the pipe for sampling concentration measurement is partially formed by a spiral tube, whereby an influence exerted on a metering part (electronic balance 23) by pipes feeding liquids from a preparation part 2 can be reduced.

Fifth Embodiment

In an automatic metal solution dilutor according to a fifth embodiment of the present invention, thicknesses (passage diameters) of two pipes having valves V2a and V2b respectively for feeding a diluent liquid to a metering hopper 21 are different from each other. A pipe branched into the two pipes according this embodiment may alternatively be branched into at least three pipes having different thicknesses.

The remaining structure of the automatic metal solution dilutor according to the fifth embodiment is substantially identical to that shown in FIG. 4. Therefore, members identical to those shown in FIG. 4 are denoted by the same reference numerals, and redundant description is not repeated.

Figure 5:
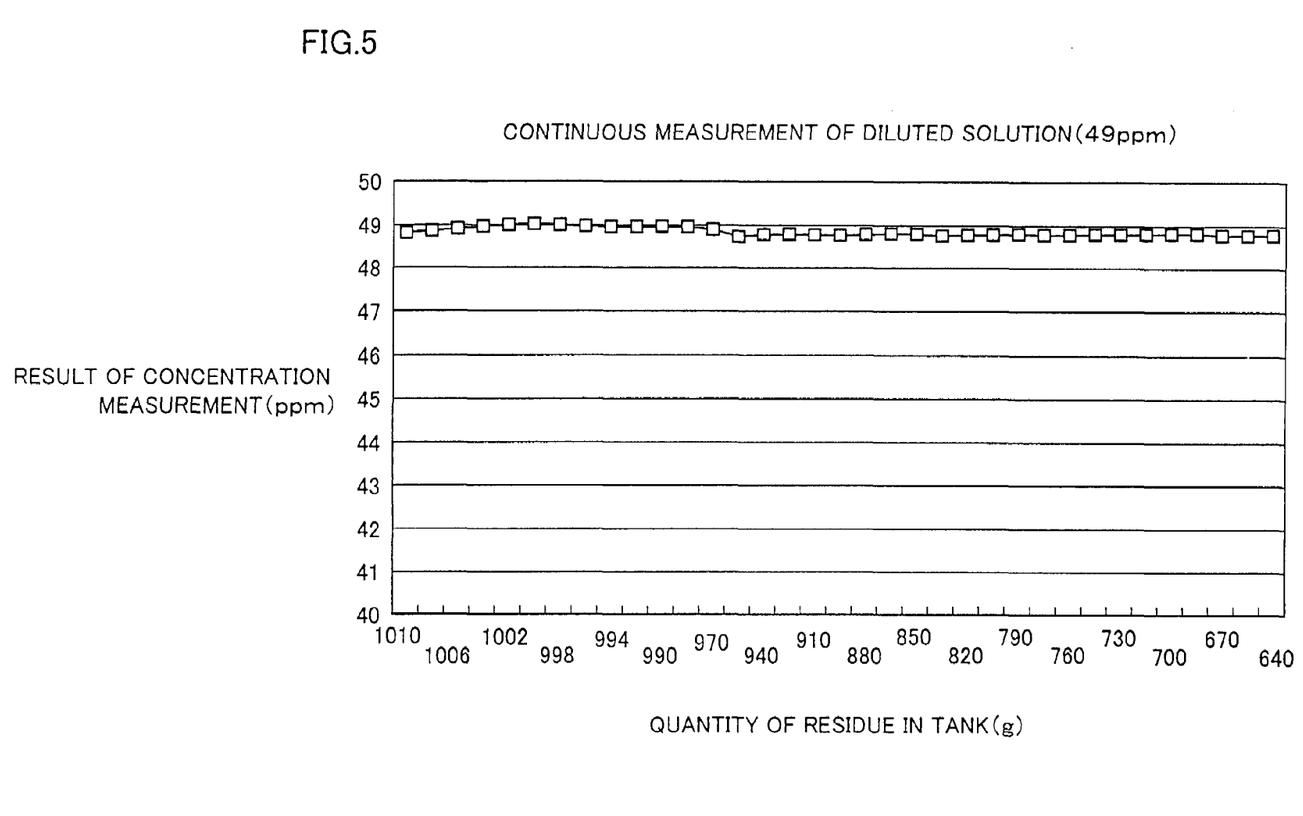
FIG. 5 illustrates the relation between the quantity and the concentration of a liquid remaining in a tank when introducing a diluent liquid into a metering hopper through at least two pipes having different thicknesses.
Figure 6:
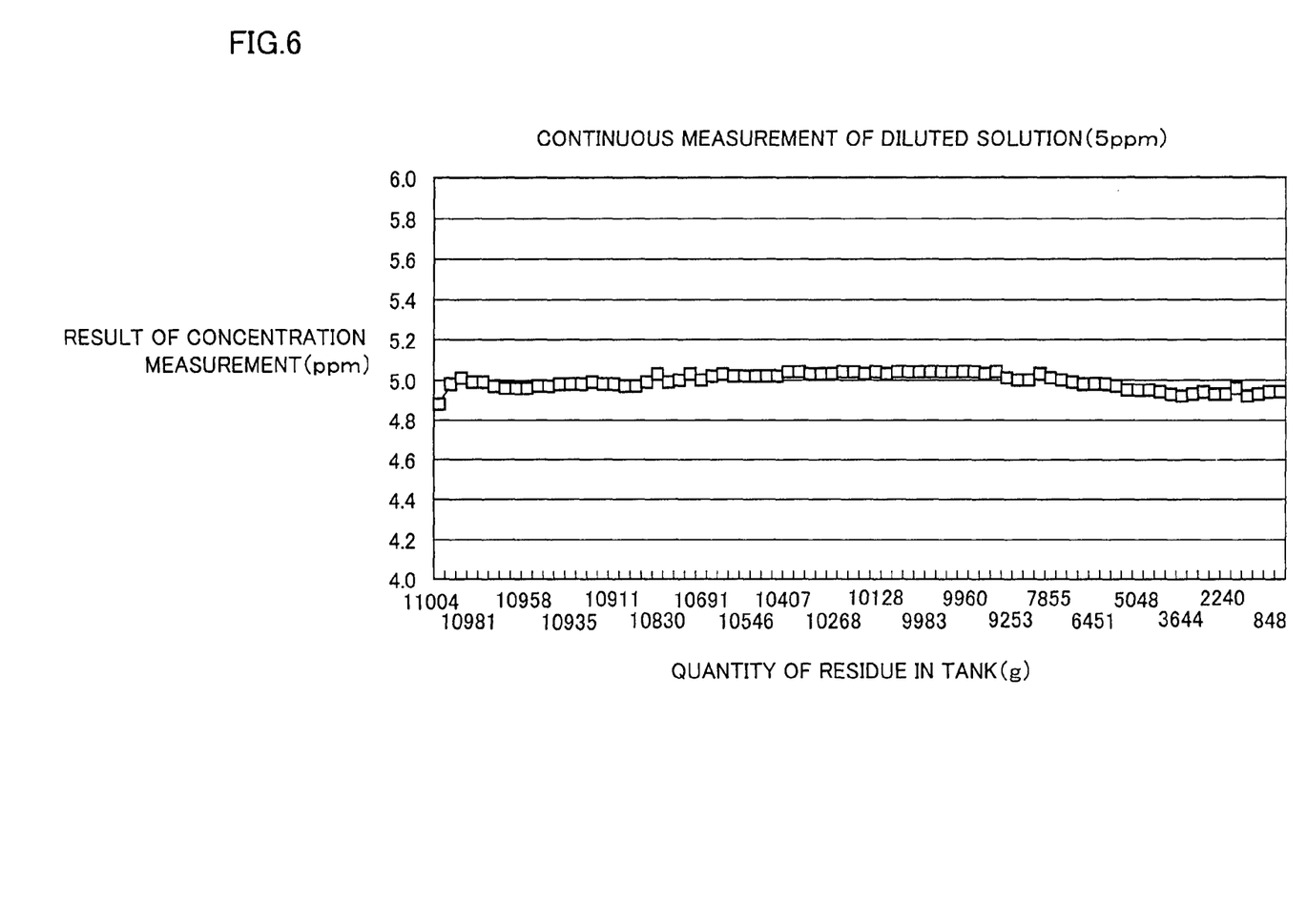
FIG. 6 illustrates the relation between the quantity and the concentration of a liquid remaining in a tank when introducing a diluent liquid into a metering hopper through at least two pipes having different thicknesses.

The inventor has investigated the relation between the quantity of a diluent liquid remaining in a tank and the concentration thereof by introducing the diluent liquid into the metering hopper 21 through at least two pipes having different thicknesses in place of stirring. FIGS. 5 and 6 show the results.

It has been recognized from the results shown in FIGS. 5 and 6 that the concentration is substantially constant at each quantity of the diluent liquid remaining in the tank.

According to the results shown in FIG. 5, the maximum, minimum and average concentrations were 49.01 ppm, 48.74 ppm and 48.83 ppm respectively, with dispersion of 0.27 ppm. According to the results shown in FIG. 6, the maximum, minimum and average concentrations were 5.04 ppm, 4.92 ppm and 4.99 ppm respectively, with dispersion of 0.12 ppm.

Sixth Embodiment

Figure 7:
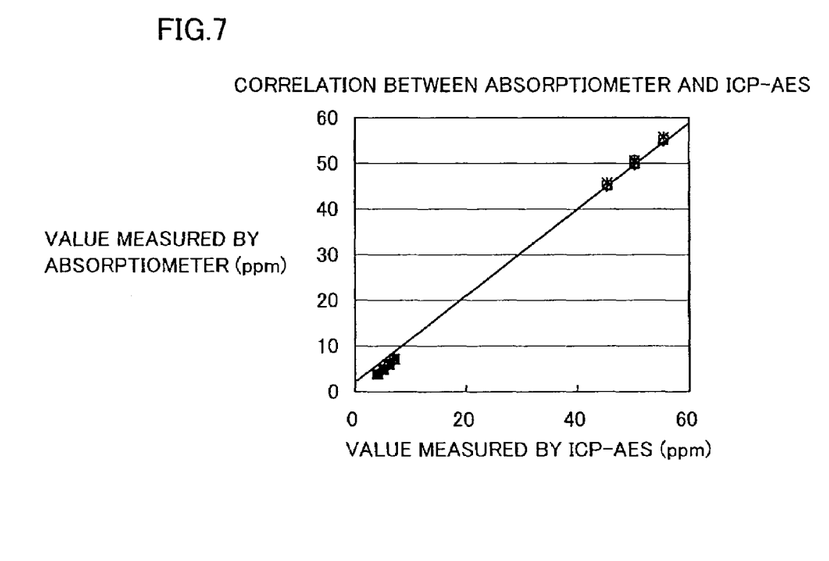
FIG. 7 illustrates measurement errors between an absorptiometer and an inductivity coupled plasma atomic spectrometer.
Figure 8:
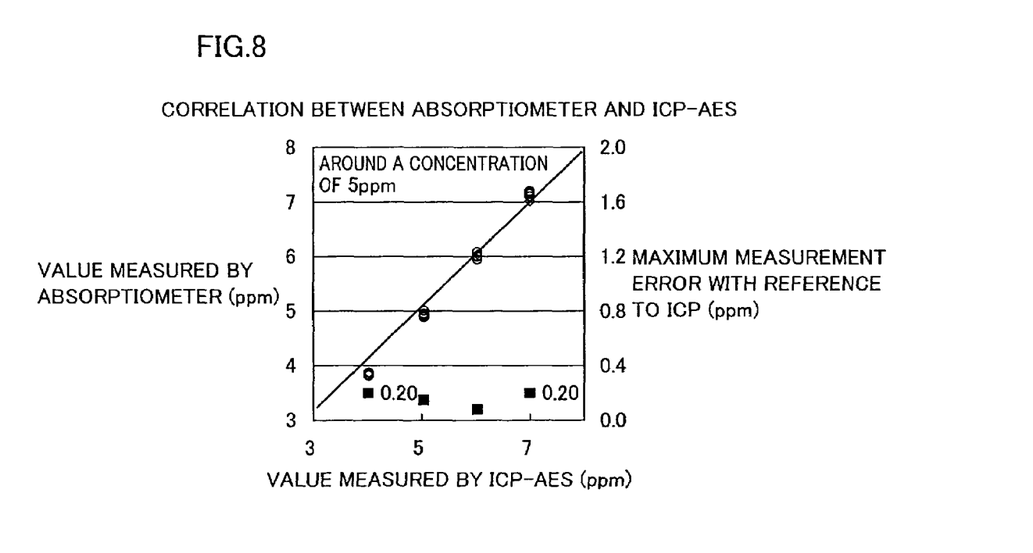
FIG. 8 illustrates measurement errors between an absorptiometer and an inductivity coupled plasma atomic spectrometer around a concentration of 5 ppm.
Figure 9:
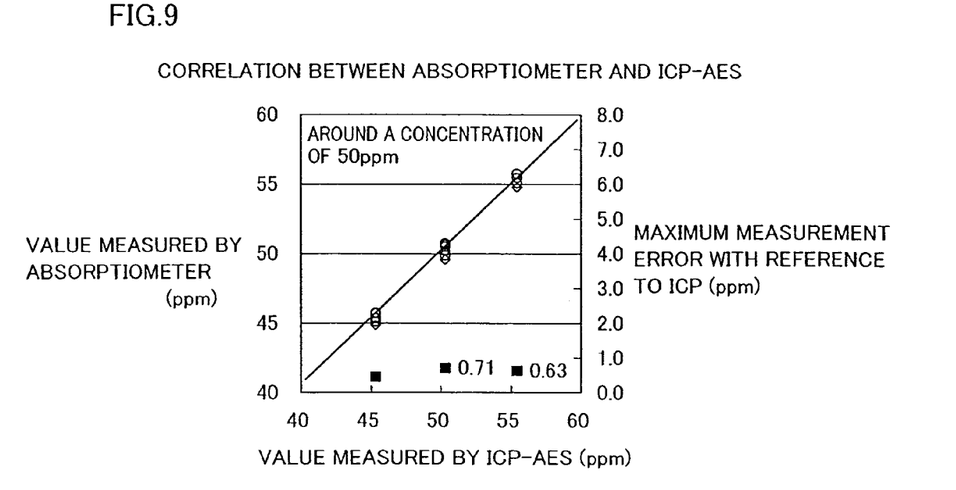
FIG. 9 illustrates measurement errors between an absorptiometer and an inductivity coupled plasma atomic spectrometer around a concentration of 50 ppm.

The inventor has verified measurement errors between an absorptiometer used in any of the aforementioned embodiments employing such a principle that the ultraviolet spectrum of an object liquid varies with the component concentration and an inductively coupled plasma-atomic emission spectroscopy (ICP-AES) measuring device. Table 1 and FIGS. 7 to 9 show the results. Referring to FIGS. 7 to 9, the results shown in Table 1 are plotted in graphs.

TABLE 1

| No. | Concentration of Sample Measured by ICP-AES (ppm) | 1 | 2 | 3 | 4 | 5 | 6 | 7 | 8 | ave | max | min | α | % RSD | Maximum Error with reference to ICP |
|---|---|---|---|---|---|---|---|---|---|---|---|---|---|---|---|
| 1 | 4.02 | 3.87 | 3.82 | 3.84 | 3.88 | 3.82 | | | | 3.85 | 3.88 | 3.82 | 0.028 | 0.73% | 0.20 |
| 2 | 5.04 | 4.93 | 4.91 | 4.92 | 5.01 | 4.89 | 4.94 | 4.93 | 4.96 | 4.94 | 5.01 | 4.89 | 0.036 | 0.73% | 0.15 |
| 3 | 6.03 | 6.04 | 6.01 | 5.95 | 6.08 | 6.00 | | | | 6.02 | 6.08 | 5.95 | 0.048 | 0.80% | 0.08 |
| 4 | 7.00 | 7.01 | 7.17 | 7.10 | 7.20 | 7.14 | | | | 7.12 | 7.20 | 7.01 | 0.074 | 1.03% | 0.20 |
| 5 | 45.30 | 44.86 | 45.11 | 45.38 | 45.70 | 45.75 | | | | 45.36 | 45.75 | 44.86 | 0.381 | 0.84% | 0.45 |
| 6 | 50.30 | 49.59 | 49.87 | 50.20 | 50.51 | 50.65 | 50.77 | | | 50.27 | 50.77 | 49.59 | 0.465 | 0.92% | 0.71 |
| 7 | 55.40 | 54.77 | 55.07 | 55.46 | 55.74 | 55.76 | | | | 55.36 | 55.76 | 54.77 | 0.432 | 0.78% | 0.63 | note) guaranteed accuracy of ICP-AES is 0.97 to 1.03 ppm (2% RSD) with reference to 1 ppm It has been recognized from the results shown in Table 1 and FIGS. 7 to 9 that the results of measurement by the absorptiometer and the ICP-AES measuring device correlate with each other in calculation of dilution accuracy and hence the absorptiometer can implement correct in-line measurement. Thus, it has been confirmable that the absorptiometer is suitable for measuring the concentration of a metal solution of the order of ppm according to the present invention.

Seventh Embodiment

The inventor has also calculated dilution accuracy with reference to an electronic balance and a load cell. The processes and results of this calculation are shown below.

Table 2 shows conditions for dilution accuracy calculation in a case of preparing a metal solution having a concentration of 5 ppm by 10 L (liters).

TABLE 2

| | |
|---|---|
| Accuracy of Electronic Balance (g) | ±0.1 |
| Load Cell Accuracy (g) | ±1 |
| Measurement Accuracy of Densitometer (ppm) | ±0.7 |
| Quantity of Extraction through Densitometer (g) | 30 |
| Pure Water Metering Accuracy (g) | ±1 |

The minimum value of the quantity of the prepared metal solution having the concentration of 5 ppm must be finally 10 L, and hence it is understood from backward calculation that 5.3 g of a stock solution (1%) is necessary. Dilution accuracy is calculated from this quantity and the conditions shown in Table 2.

(1) Introduction of Stock Solution

When a result of metering of the stock solution of 5.3 g is 5.30 g, the metal quantity in the stock solution is as follows:

$$(5.30±0.1/100)=0.0530 \text{ g}±0.001 \text{ g}$$

(2) First Dilution

In order to finish a diluted solution with concentration of 50 ppm in first dilution, pure water is added to the stock solution for preparing a solution of 1060 g. At this time, the concentration of the solution is as follows:

$$(5.30±0.1)/100/(1060±1)=50 \text{ ppm}±0.7 \text{ ppm}$$

After the solution is consumed by 30 g through measurement with a densitometer, the metal quantity in the solution is calculated through a value measured with the balance as follows:

$$(1060-30+1)×(0.000050±0.00000007)=0.0515 \text{ g}+0.0017 \text{ g}$$

(3) Second (Final) Dilution

Then, the calculated value is fed back for finishing the diluted solution to 10300 g (10.3 L) so that the final dilution concentration reaches 5 ppm in consideration of dispersion in quantity of preparation. The final dilution concentration and accuracy are as follows:

$$(0.0515±0.0017)/(10300±1)=5 \text{ ppm}±0.17 \text{ ppm}$$

When dilution accuracy with a load cell is calculated in a similar manner to the above, the final dilution concentration and accuracy reach 5 ppm±1.02 ppm. It is confirmable that the electronic balance can perform dilution of higher quality as compared with the load cell in calculation.

However, influences are additionally exerted by liquids remaining in a tank and pipes, time change of a sensor and a measuring device and the like.

In each of the aforementioned embodiments, the material for portions coming into contact with the stock solution, the diluent liquid and the diluted solution preferably consists of fluororesin. The fluororesin is preferably prepared from polytetrafluoroethylene (PTFE) or a tetrafluoroethylene-perfluoro alkyl vinyl ether copolymer (PFA), and preferably mainly composed of Super-PFA having a reduced fluorine content in particular. Thus, the solution, the diluent liquid and the diluted solution come into contact with no metal portion, whereby the quantity of metal contaminants can be reduced suitably for metal dilution of the order of ppm.

According to the inventive automatic metal solution dilutor, as hereinabove described, it is possible to correctly dilute a concentrated liquid (stock solution) of the order of percentage to a metal solution of the order of ppm having a required quantity and a required concentration with no dilution error by measuring the absorbance of a diluted solution in the dilution tank and metering the diluted solution in the dilution tank with the electronic balance of the metering device so that the dilution magnification reaches a prescribed value on the basis of the measured absorbance.

The control part monitors the values measured by the measuring device and metered by the metering device respectively for operating and controlling the quantities of the stock solution and the diluent liquid fed to the dilution tank on the basis thereof, whereby it is possible to continuously and automatically measure and monitor the dilution magnification and the quantity of preparation.

The concentration of the diluted solution, which is measured with the absorptiometer manufacturable at a low cost, may not be subjected to off-line testing with a high-quality analyzer such as a high-priced atomic absorption spectrophotometer or an ICP analyzer. Further, the electronic balance enables metering with resolution higher than that of a load cell by at least one digit due to weighing.

Thus, it is possible to provide an automatic dilutor implementing accurate dilution of a metal solution at a low cost.

Further, a specified quantity of the stock solution is diluted according to a gravimetric method, whereby no error results from fluctuation of the liquid temperature but anybody can accurately dilute the stock solution with no requirement for experiences and skillfulness dissimilarly to a manual operation. Thus, the dilutor causes no human error and the concentration and the results of weighing and measurement can be readily confirmed due to monitor display with a required concentration and a required quantity while it is possible to prepare a diluted solution with a concentration and a quantity required by the feeder side, whereby the feeder side can effectively take flexible countermeasures.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An automatic metal solution dilutor comprising:
    a material feeding part storing a stock solution to be diluted;
    a dilution tank mixing said stock solution fed from said material feeding part with a diluent liquid and preparing a diluted solution for diluting said stock solution, said dilution tank having a purging mechanism incorporating compressive gas inward and discharging said compressive gas outward;
    a measuring device measuring absorbance of said diluted solution in said dilution tank;
    a metering device metering said diluted solution in said dilution tank with an electronic balance so that a dilution magnification obtained from said absorbance measured by said measuring device reaches a prescribed value;
    a control part monitoring the value measured by said measuring device and the value metered by said metering device for operating and controlling the quantity of at least either said stock solution or said diluent liquid fed to said dilution tank so that said dilution magnification reaches said prescribed value on the basis of said absorbance measured by said measuring device, and
    a hopper having said purging mechanism incorporating said compressive gas inward and discharging said compressive gas outward in a path for feeding said diluted solution from said dilution tank, wherein a pipe connecting said dilution tank and said measuring device with each other is at least partially formed by a spiral tube.

2. The automatic metal solution dilutor according to claim 1, further comprising
    a finishing part having several closed tanks including mechanisms for storing said diluted
        solution fed from said dilution tank and feeding said diluted solution with compressed gas.

3. The automatic metal solution dilutor according to claim 1, wherein said material feeding part includes an exchangeable bottle for storing said stock solution and has a structure feeding said stock solution stored in said bottle to said dilution tank with compressed gas.

4. The automatic metal solution dilutor according to claim 1, wherein at least two pipes having different thicknesses introduce said diluent liquid into said dilution tank.

5. The automatic metal solution dilutor according to claim 1, wherein all portions of said dilutor that come into contact with said stock solution, said diluent liquid and/or said diluted solution are formed of a material consisting of resin containing a low amount of fluorine.

* * * * *